(12) United States Patent
Pinder

(10) Patent No.: US 10,104,507 B1
(45) Date of Patent: Oct. 16, 2018

(54) SYSTEMS AND METHODS TO LOCATE AND OPERATE A PORTABLE DEVICE ON SMART CLOTHING

(71) Applicant: MOTOROLA SOLUTIONS, INC., Chicago, IL (US)

(72) Inventor: Ellis A. Pinder, Davie, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/588,513

(22) Filed: May 5, 2017

(51) Int. Cl.
| | |
|---|---|
| *H03G 3/02* | (2006.01) |
| *H04B 1/401* | (2015.01) |
| *A61N 1/00* | (2006.01) |
| *A61B 5/04* | (2006.01) |
| *G06K 19/07* | (2006.01) |
| *G06K 7/10* | (2006.01) |
| *H04W 4/02* | (2018.01) |
| *H04R 1/40* | (2006.01) |
| *H04R 3/00* | (2006.01) |
| *H04R 1/02* | (2006.01) |
| *H04R 3/04* | (2006.01) |
| *H04W 88/06* | (2009.01) |

(52) U.S. Cl.
CPC .............. *H04W 4/026* (2013.01); *H03G 3/02* (2013.01); *H04B 1/401* (2013.01); *H04R 1/028* (2013.01); *H04R 1/406* (2013.01); *H04R 3/005* (2013.01); *H04R 3/04* (2013.01); *H04W 4/023* (2013.01); *H04R 2201/023* (2013.01); *H04R 2201/403* (2013.01); *H04W 88/06* (2013.01)

(58) Field of Classification Search
CPC ......... H04W 4/026; H03G 3/02; H04B 1/401; H04R 1/028; H04R 1/406; H04R 3/005

USPC ................................ 340/8.1; 607/5; 600/505
See application file for complete search history.

(56) References Cited

U.S. PATENT DOCUMENTS

| | | | |
|---|---|---|---|
| 6,563,424 B1 | 5/2003 | Kaario | |
| 6,853,303 B2 | 2/2005 | Chen et al. | |
| 8,290,545 B2 | 10/2012 | Terlizzi | |
| 9,082,025 B2* | 7/2015 | Fastert | G06K 19/027 |
| 9,380,855 B2 | 7/2016 | Anderson | |
| 9,473,188 B2 | 10/2016 | Corretjer et al. | |
| 9,931,050 B2* | 4/2018 | Kaib | A61B 5/0468 |

(Continued)

OTHER PUBLICATIONS

HTC Corporation, "HTC One (M8) Motion Gestures," website (2011-2017) 5 pages, USA, httb://www.hte.corm/us/support/htc-one-m8/howto/464882.html.

(Continued)

*Primary Examiner* — Nam V Nguyen
(74) *Attorney, Agent, or Firm* — Michael Best & Friedrich LLP

(57) ABSTRACT

Systems and methods locating and operating a portable device mounted to a garment. One method includes receiving, with an electronic processor, a signal from a communication line of a plurality of communication lines integrated within the garment. The method also includes determining, with the electronic processor, a location, on the garment, of the portable device based on the signal. The method also includes determining, with the electronic processor, an operational mode for the portable device based on the location. The method also includes adjusting, with the electronic processor, operation of the portable device based on the operational mode.

20 Claims, 6 Drawing Sheets

(56) References Cited

U.S. PATENT DOCUMENTS

| | | | |
|---|---|---|---|
| 2003/0193399 A1* | 10/2003 | Hum | G06K 7/0008 |
| | | | 340/573.4 |
| 2008/0254822 A1 | 10/2008 | Tilley | |
| 2014/0318699 A1 | 10/2014 | Longinotti-Buitoni et al. | |
| 2015/0370320 A1 | 12/2015 | Connor | |
| 2016/0094936 A1 | 3/2016 | Yang et al. | |
| 2016/0128632 A1* | 5/2016 | Wiebe | A61B 5/0015 |
| | | | 340/870.07 |
| 2016/0249174 A1 | 8/2016 | Patel et al. | |
| 2017/0127274 A1 | 5/2017 | Lin et al. | |
| 2017/0143977 A1* | 5/2017 | Kaib | A41D 13/1281 |
| 2018/0092415 A1* | 4/2018 | Rider | A41D 31/0033 |

OTHER PUBLICATIONS

PCT/US2018/030265 International Search Report and Written Opinion of the International Searching Authority dated Aug. 16, 2018 (13 pages).

\* cited by examiner

HORIZONTAL FIBER PATH ————————
VERTICAL FIBER PATH — — — — —

SYSTEMS AND METHODS TO LOCATE AND OPERATE A PORTABLE DEVICE ON SMART CLOTHING

BACKGROUND OF THE INVENTION

A portable device, such as a portable communication device, a portable camera, and the like, may be mounted to a garment, such as a vest, worn by a user of the portable device. The portable device may be mounted to the garment at different locations on the garment. For example, when the portable device is a portable radio, the portable radio may be mounted to the garment so that the portable radio is within close proximity of a user's mouth and ear. In such instances, the portable radio may be mounted to the garment at a location on the garment associated with a user's chest or shoulder. When the portable device is a portable camera, the portable camera may be mounted to the garment based on the desired viewing direction (for example, a forward viewing direction, a rear viewing direction, and the like). In such instances, the portable camera may be mounted to the garment at a location on the garment associated with a user's front for a forward viewing direction or at a location on the garment associated with a user's back for a rear viewing direction.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
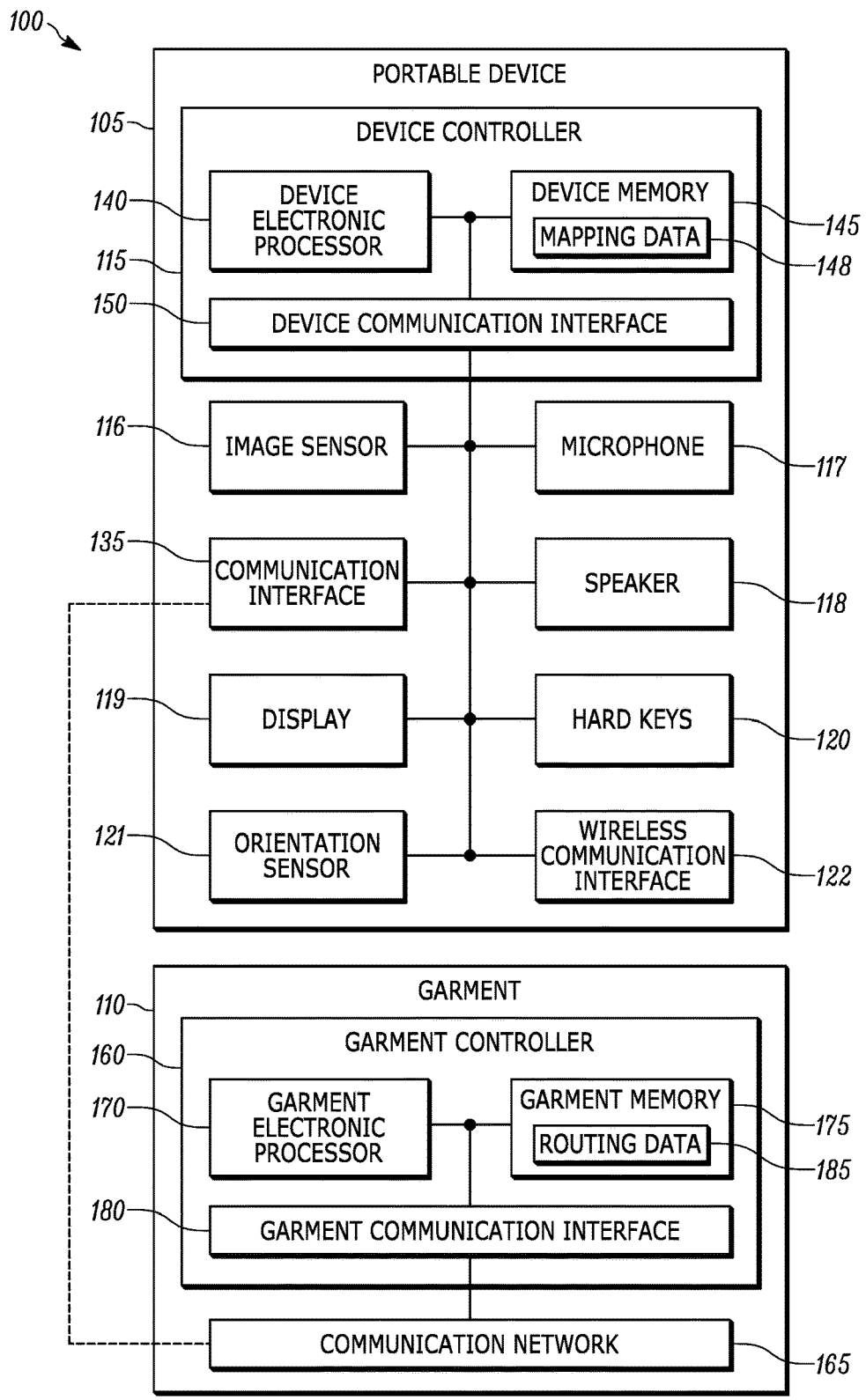
FIG. 1 is a diagram of a system for locating and operating a portable device mounted on a garment according to one embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

One embodiment provides a method for locating and operating a portable device mounted to a garment. The method includes receiving, with an electronic processor, a signal from a communication line of a plurality of communication lines integrated within the garment. The method also includes determining, with the electronic processor, a location, on the garment, of the portable device based on the signal. The method also includes determining, with the electronic processor, an operational mode for the portable device based on the location. The method also includes adjusting, with the electronic processor, operation of the portable device based on the operational mode.

Another embodiment provides a portable device mounted to a garment. The portable device includes a memory storing instructions. The portable device also includes an electronic processor that is coupled to the memory and, through execution of the instructions, is configured to receive a signal from a communication line of a plurality of communication lines integrated within the garment. The electronic processor is also configured to determine a location, on the garment, of the portable device based on the signal. The electronic processor is also configured to determine an operational mode for the portable device based on the location. The electronic processor is also configured to adjust operation of the portable device based on the operational mode.

Another embodiment provides a system for locating and operating a portable device. The system includes a garment having a communication line of a plurality of communication lines integrated within the garment. The garment includes an electronic processor configured to generate and transmit a signal. The system also includes a portable device mounted to the garment. The portable device includes a second electronic processor configured to receive the signal from the communication line integrated within the garment. The second electronic processor is also configured to determine a location, on the garment, of the portable device based on the signal. The second electronic processor is also configured to determine an operational mode for the portable device based on the location. The second electronic processor is also configured to adjust operation of the portable device based on the operational mode.

FIG. 1 is a diagram of a system 100 for locating and operating a portable device 105 mounted on a garment 110 according to one embodiment. In the example illustrated, the system 100 includes the portable device 105 and the garment 110. The portable device 105 may be a handheld communication device, for example, a mobile telephone, a mobile radio, a smart watch, or other smart wearable. Alternatively or in addition, the portable device 105 may be a camera device, for example, a mobile camera or other portable image recording device. The garment 110 is a wearable body garment, such as a vest, a pair of pants, or a jacket. As noted above, the portable device 105 may be mountable to the garment 110. The portable device 105 may be mounted to the garment 110 using, for example, a hook and loop fastener, a snap on fastener, a button, or other type of mechanical attachment mechanism. In some embodiments, the garment 110 is worn by a public safety officer or first responder, such as a police officer. In some embodiments, the system 100 includes more or fewer devices 105 and garments 110 than illustrated in FIG. 1.

In the example illustrated, the portable device 105 includes a device controller 115, an image sensor 116, a microphone 117, a speaker 118, a display 119, hard keys 120, an orientation sensor 121, a wireless communication interface 122, and a communication interface 135. The device controller 115, the image sensor 116, the microphone 117, the speaker 118, the display 119, the hard keys 120, the orientation sensor 121, the wireless communication interface 122, and the communication interface 135 communicate over one or more control or data connections or buses. In some embodiments, the portable device 105 includes fewer or additional components in configurations different from that illustrated in FIG. 1. For example, depending on the desired functionality of the portable device 105, the portable device 105 may include additional or fewer image sensors, microphones, speakers, displays, hard keys, orientation sensors, and communication interfaces.

The microphone 117, the speaker 118, and the wireless communication interface 122 allow the portable device 105 to function as a mobile communication device, such as a portable radio. For example, the microphone 117 captures audio, the speaker 118 generates audio, and the wireless communication interface 122 establishes a bi-directional communication link with one or more wireless communication networks. The image sensor 116 is configured to collect visual data. For example, in some embodiments, the image sensor 116 is a camera, which allows the portable device 105 to function as a mobile camera. The display 119 is configured to provide output to and receive input from a user of the portable device 105. For example, in some embodiments, the display 119 is a touchscreen display that includes one or more reconfigurable soft keys for receiving input from a user of the portable device 105. The hard keys 120 are configured to receive input from a user of the portable device 105. In some embodiments, the hard keys 120 are reconfigurable. For example, the user of the portable device 105 may reconfigure the hard keys 120 using the display 119. The hard keys 120 and the soft keys are configured to receive user input that controls the functions of the portable device 105, such as to dial a phone number, alter a volume setting, select a radio channel for communication, begin audio or video recording, and the like. The orientation sensor 121 detects an orientation of the portable device 105, such as right-side up, upside down, and the like. For example, the orientation sensor 121 may detect when the portable device 105 is mounted upside down on the garment 110.

The communication interface 135 is configured to receive one or more signals from the garment 110. In some embodiments, the communication interface 135 is a radio-frequency (RF) communication interface. When the communication interface 135 is an RF communication interface, the communication interface 135 includes an antenna. The antenna is configured to receive the one or more signals from the garment 110. In some embodiments, the communication interface 135 is an optical communication interface. When the communication interface 135 is an optical communication interface, the communication interface 135 includes an optical sensor configured to detect optical signals transmitted from the garment 110. In some embodiments, the communication interface 135 is an inductive communication interface. When the communication interface 135 is an inductive communication interface, the communication interface 135 includes an inductor. In some embodiments, the communication interface 135 is a conductive communication interface. When the communication interface 135 is a conductive communication interface, the communication interface 135 includes one or more terminals that physically connect with the garment 110. The one or more terminals of the communication interface 135, when physically connected with the garment 110, are configured to receive the one or more signals from the garment 110. Whether the communication interface 135 is an RF communication interface, an optical communication interface, or a conductive communication interface corresponds to the type of communication network of the garment 110. In some embodiments, the communication interface 135 includes two or more of an RF communication interface, an optical communication interface, and a conductive communication interface.

The device controller 115 includes combinations of hardware and software that are operable to, among other things, identify a location, on the garment 110, of the portable device 105 and adjust the operation of the portable device 105 based on the identified location. In the example illustrated, the device controller 115 includes a device electronic processor 140 (for example, a microprocessor or other suitable device), a device memory 145, and a device communication interface 150. The device electronic processor 140, the device memory 145, and the device communication interface 150 communicate over one or more control or data connections or buses. In some embodiments, the device controller 115 includes fewer or additional components in configurations different from that illustrated in FIG. 1. In some embodiments, the device controller 115 performs additional functionality than the functionality described herein.

The device electronic processor 140 is configured to retrieve, from the device memory 145, instructions related to the methods described herein. The device electronic processor 140 is also configured to execute those instructions to implement the functionality of the portable device 105 described herein. The device memory 145 is an example of a non-transitory computer readable medium and may include, for example, a program storage area and a data storage area. The program storage area and the data storage area may include combinations of different types of memory, including read only memory (ROM) and random access memory (RAM). The instructions may include one or more applications, program data, filters, rules, one or more program modules, and other executable instructions.

In the example illustrated, the device memory 145 stores mapping data 148. The mapping data 148 may include, for example, a lookup table. As described in greater detail below, the device controller 115 uses the mapping data 148 for mapping the one or more signals received from the garment 110 to one or more physical locations on the garment 110, to one or more communication lines among a plurality of communication lines integrated within the garment 110, or a combination thereof.

The device communication interface 150 allows the device controller 115 (and its components) to communicate with external devices and various input and output devices, such as the image sensor 116, the microphone 117, the communication interface 135, the speaker 118, the display 119, the hard keys 120, the orientation sensor 121, and the wireless communication interface 122. As noted above, the image sensor 116, the microphone 117, the communication interface 135, the speaker 118, the display 119, the hard keys 120, the orientation sensor 121, and the wireless communication interface 122 allow for a desired functionality of the portable device 105, such as communication functionality, imaging functionality, and the like.

In the example illustrated, the garment 110 includes a garment controller 160 and a communication network 165. In some embodiments, the garment 110 includes fewer or additional components in configurations different from that illustrated in FIG. 1.

The garment controller 160 includes combinations of hardware and software that are operable to, among other things, generate and transmit signals to the portable device 105 via the communication network 165. In the example illustrated, the garment controller 160 includes a garment electronic processor 170 (for example, a microprocessor or other suitable device), a garment memory 175, and a garment communication interface 180. The garment electronic processor 170, the garment memory 175, and the garment communication interface 180 communicate over one or more control or data connections or buses. In some embodiments, the garment controller 160 includes fewer or additional components in configurations different from that illustrated in FIG. 1. In some embodiments, the garment controller 160 performs additional functionality than the functionality described herein.

The garment electronic processor 170 is configured to retrieve, from the garment memory 175, instructions related to methods described herein. The garment electronic processor 170 is also configured to execute those instructions to implement the functionality of the garment 110 described herein. The garment memory 175 is an example of a non-transitory computer readable medium and may include, for example, a program storage area and a data storage area. The program storage area and the data storage area may include combinations of different types of memory, including read only memory (ROM) and random access memory (RAM). The instructions may include one or more applications, program data, filters, rules, one or more program modules, and other executable instructions.

In the example illustrated, the garment memory 175 stores routing data 185. The routing data 185 may include, for example, a mapping of physical locations, a plurality of communication lines, or a combination thereof on the garment 110 to a plurality of unique identifiers. In some embodiments, the garment electronic processor 170 accesses the routing data 185 to generate the one or more signals for transmission (via the communication network 165) to the portable device 105 for determining a location, on the garment 110, of the portable device 105.

The garment communication interface 180 allows the garment controller 160 (and its components) to communicate with external devices and various input and output devices. In the example shown, the garment controller 160 communicates with the communication network 165 through the garment communication interface 180. For example, the garment controller 160 may transmit a generated signal to the communication network 165 via the garment communication interface 180.

Figure 2:
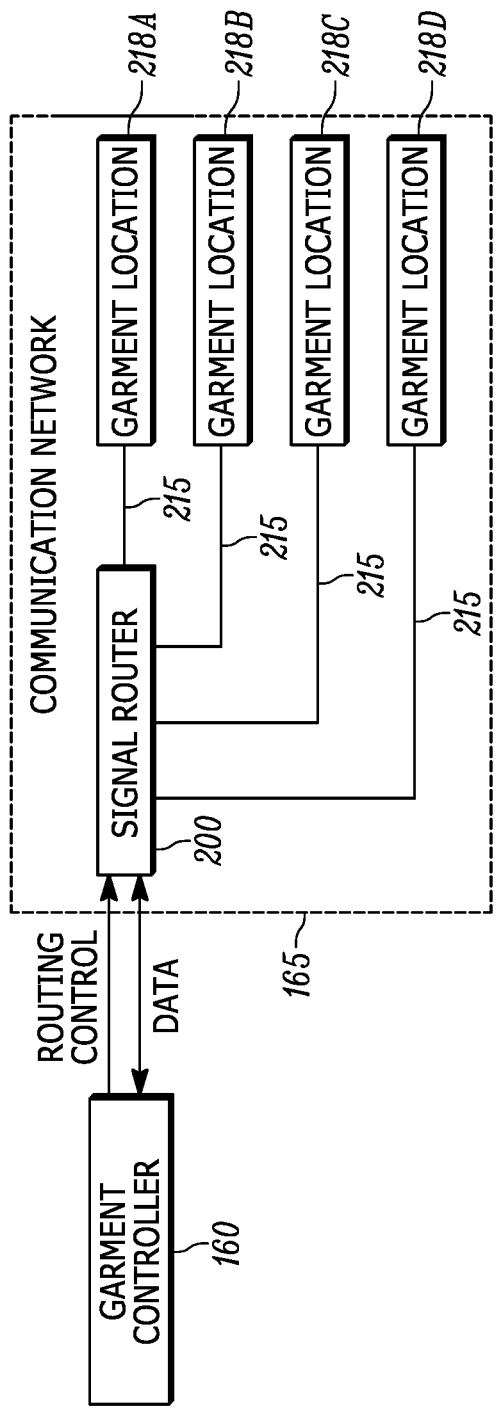
FIG. 2 is a diagram of a communication network of the garment included in the system of FIG. 1 according to one embodiment.

The communication network 165 is configured to receive the one or more signals from the garment controller 160 and transmit the one or more signals to the communication interface 135 of the portable device 105. FIG. 2 is a diagram of the communication network 165 of the garment 110 included in the system 100 of FIG. 1 according to one embodiment. In the example illustrated, the communication network 165 includes a signal router 200. The signal router 200 is configured to control the routing of the one or more signals received from the garment controller 160 to one or more of the communication lines 215. The signal router 200 is a control circuit including hardware circuitry, software, or a combination thereof to implement the routing functionality.

The communication network 165 also includes a plurality of communication lines 215 (referred to herein as "the communication lines 215" or individually as "a communication line 215"). The communication lines 215 are configured to communicate the one or more signals received from the signal router 200 to the communication interface 135 of the portable device 105. In some embodiments, the communication lines 215 are integrated within the garment 110. For example, the communication lines 215 may be positioned between one or more fabric layers of the garment 110, woven into a fabric layer of the garment 110, or adhered to the fabric of the garment 110. Additionally, in the example illustrated, each of the communication lines 215 is associated with one of a plurality of garment locations 218A, 218B, 218C, and 218 D. In the following description, when referencing any one of the garment locations 218A through 218D, a reference to the garment location 218 is used and when referencing the garment locations 218A through 218D collectively, a reference to the garment locations 218 is used. In some embodiments, the communication network 165 includes more or fewer garment locations and communication lines than illustrated in FIG. 2.

As noted above, the portable device 105 is mountable to the garment 110. The portable device 105 may be mounted to the garment 110 using an attachment mechanism of the garment 110. Accordingly, each attachment mechanism of the garment 110 may correspond to one of the garment locations 218. In other words, an attachment mechanism of the garment 110 may be positioned at each of the garment locations 218.

The communication network 165 may be, for example, an optical communication network, a conductive communication network, an inductive communication network, an RF communication network, and the like. When the communication network 165 is an optical communication network, the communication lines 215 may be optical communication lines configured to carry one or more optical signals to a garment location 218. Additionally, the communication network 165 may include optical shielding enclosing each of the communication lines 215. The optical shielding may enclose each of the communication lines 215 between the garment controller 160 and a garment location 218. An optical output terminal or lack of optical shielding (exposed portion of the optical communication line 215) may be provided at the garment location 218 for receipt by the communication interface 135 of the portable device 105. When the communication network 165 is an inductive communication network, the communication lines 215 may be embedded electrical lines configured to carry one or more current signals to the garment location 218. Additionally, when the communication network 165 is an inductive communication network, the communication lines 215 may induce current in an inductor of the communication interface 135. When the communication network 165 is a conductive communication network, the communication lines 215 may be embedded electrical lines configured to carry one or more current signals to the garment location 218. When the communication network 165 is an RF communication network, the communication lines 215 may be embedded electrical lines configured to carry an electrical signal to an antenna associated with a garment location 218. Additionally, when the communication network 165 is an RF communication network, the communication lines 215 may themselves act as antennas. As noted above, the communication interface 135 of the portable device 105 corresponds to the type of communication network 165 to receive signals sent by the garment controller 160.

In some embodiments, the communication lines 215 conductively couple the portable device 105 and the garment 110. For example, the garment 110 may include a plurality of metal contacts where each of the metal contacts is coupled to a communication line 215 and is positioned at a garment location 218. Additionally, the communication interface 135 of the portable device 105 may include a metal contact that conductively couples to a conductive contact associated with a communication line 215. Accordingly, when the portable device 105 is conductively coupled to a communication line 215 (via the metal contacts), the portable device 105 may receive one or more signals from the garment 110 via the communication network 165. As the garment locations 218 are points at which the portable device 105 may interface with the garment 110 via the communication interface 135 and the communication lines 215, the garment locations 218 may also be referred to as interface points.

Figure 3:
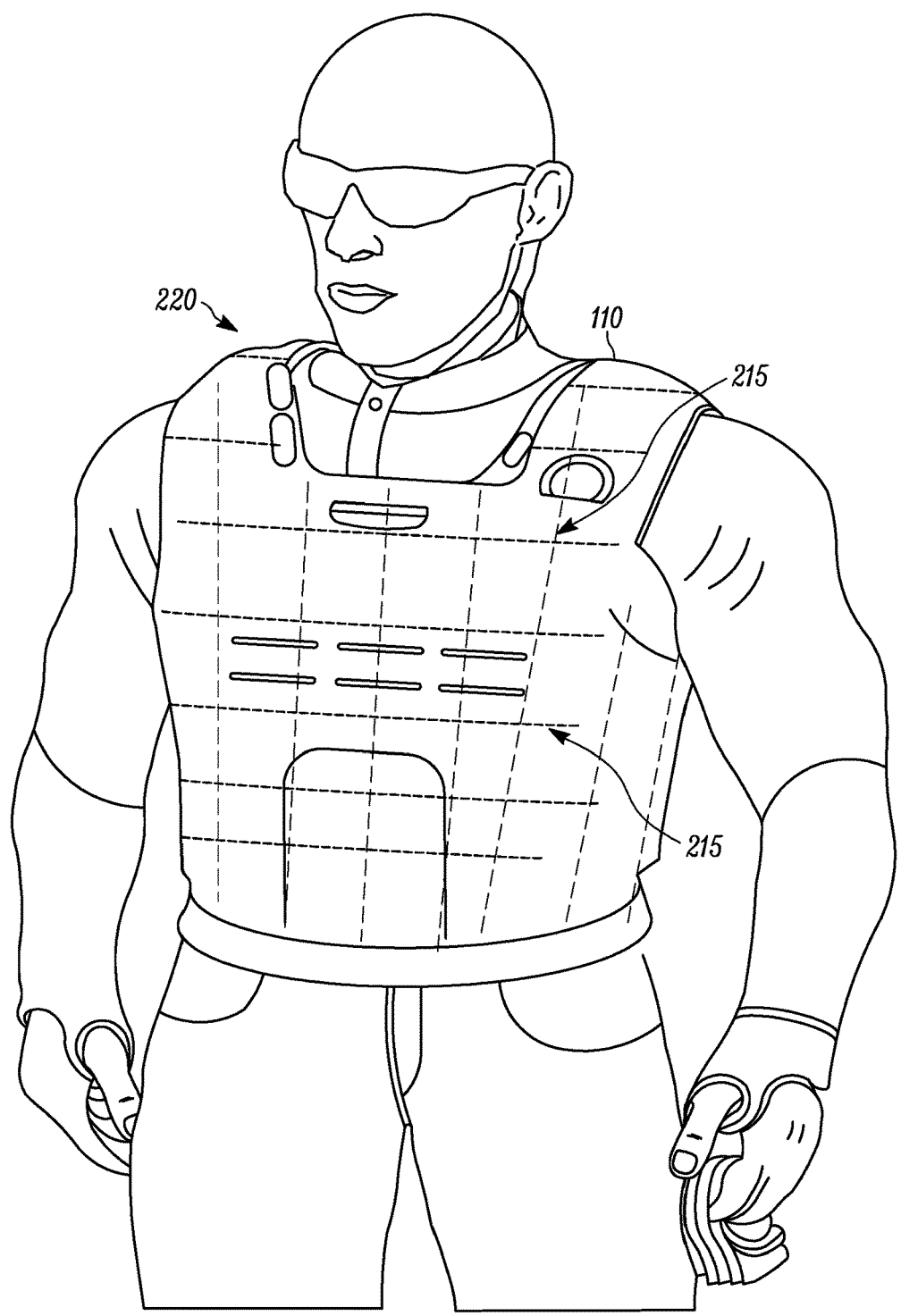
FIG. 3 is an illustration of the garment with a plurality of communication lines included in the communication network of FIG. 2 according to one embodiment.

In some embodiments, the communication lines 215 of the communication network 165 are arranged in a coordinate system 220 on the garment 110, as illustrated in FIG. 3. In the example illustrated, the communication lines 215 are horizontally integrated within the garment 110 and vertically integrated within the garment 110. Accordingly, the communication lines 215 that are horizontally integrated within the garment 110 are associated with an x-axis of the coordinate system 220 while the communication lines 215 that are vertically integrated within the garment 110 are associated with a y-axis of the coordinate system 220.

Figure 4:
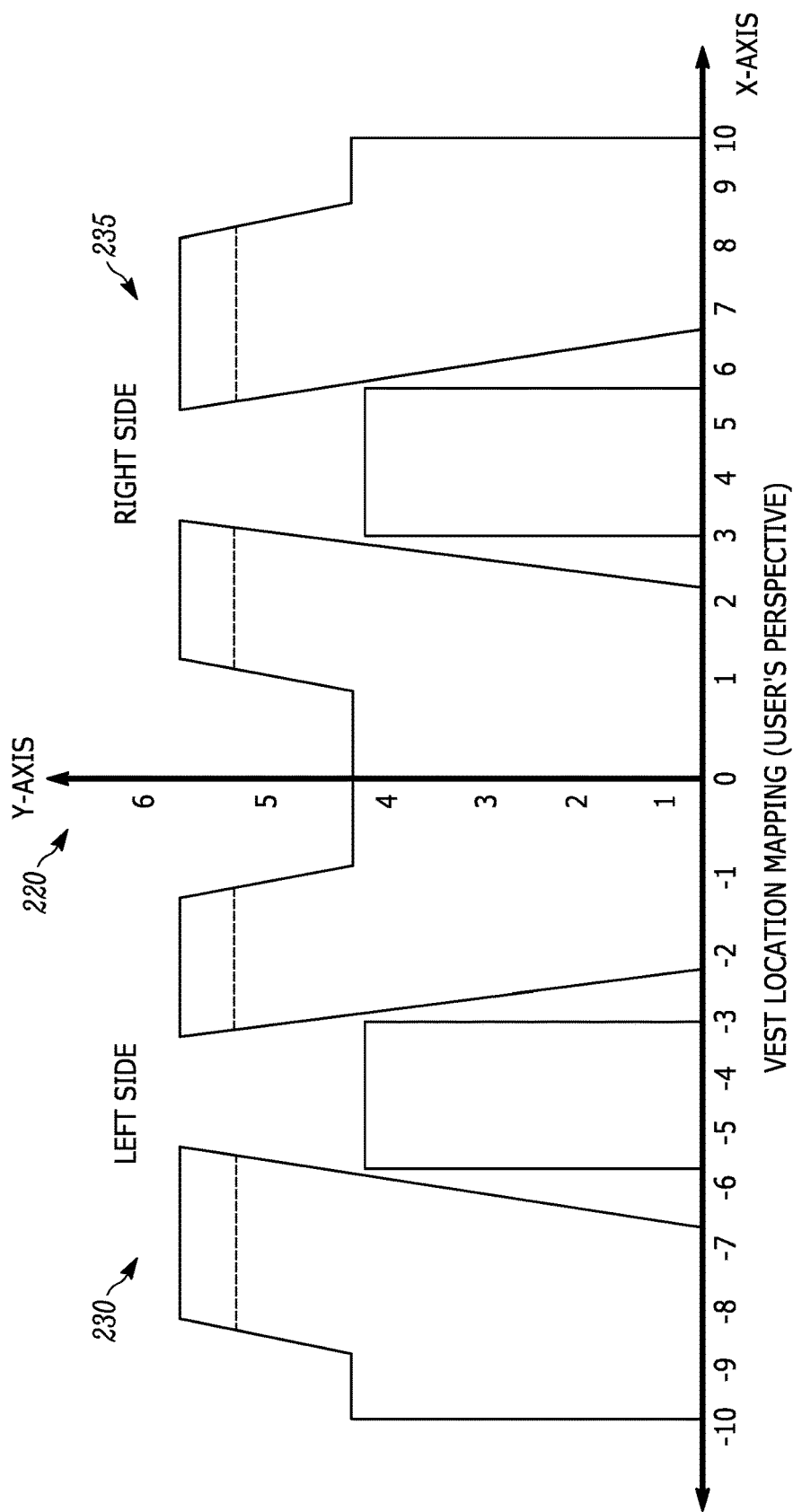
FIG. 4 is a diagram of each surface of the garment associated with the coordinate system formed by the plurality of communication lines illustrated in FIG. 3 according to one embodiment.

When the communication lines 215 of the communication network 165 are arranged in the coordinate system 220 on the garment 110, the garment 110, which is not two-dimensional, may be unfolded diagrammatically to map the three-dimensional garment 110 to the two-dimensional coordinate system 220. For example, as illustrated in FIG. 4, a bottom, center, front of the garment 110 may be positioned at an origin (0, 0) of the coordinate system 220 while a left side 230 of the garment 110 is positioned along a negative x-axis of the coordinate system 220 and a right side 235 of the garment 110 is positioned along a positive x-axis of the coordinate system 220. In other embodiments, a different portion of the garment 110 is positioned at the origin (0, 0) of the coordinate system 220.

Figure 5:
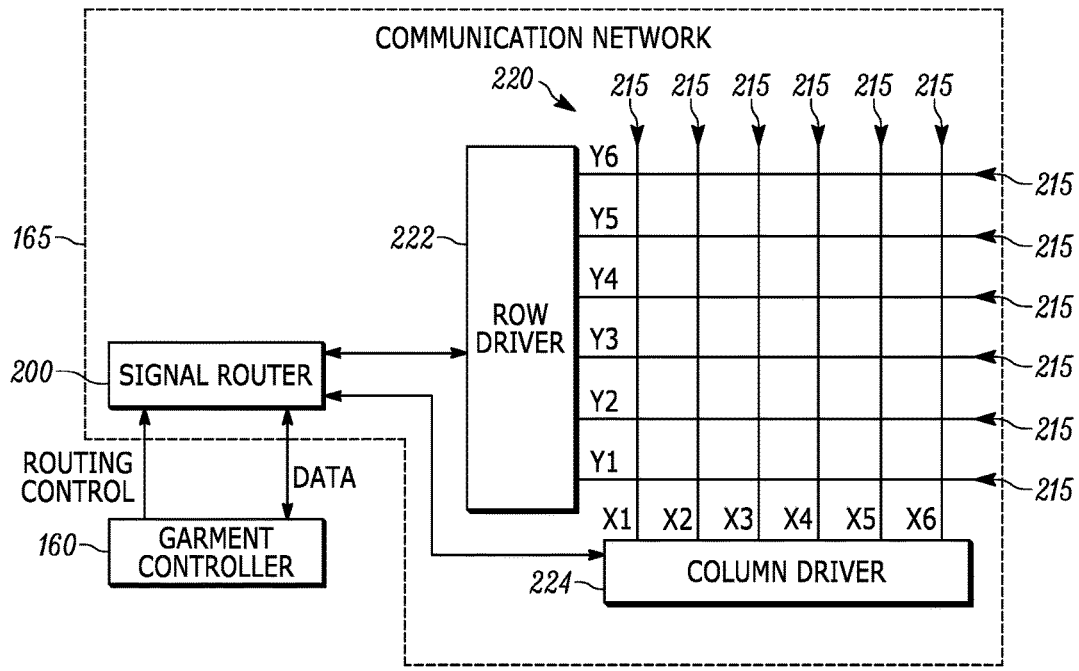
FIG. 5 is a diagram of a communication network of the garment included in the system of FIG. 1 when the communication network forms a coordinate system according to one embodiment.

FIG. 5 is a diagram of the communication network 165 of the garment 110 included in the system 100 of FIG. 1 when the communication lines 215 are arranged in the coordinate system 220 on the garment 110 according to one embodiment. In the example illustrated, the communication network 165 includes the signal router 200, a row driver 222, a column driver 224, and the communication lines 215 arranged in the coordinate system 220. The signal router 200, the row driver 222, and the column driver 224 communicate over one or more control or data connections or buses. When the communication lines 215 are arranged in the coordinate system 220, the signal router 200 routes the one or more signals received from the garment controller 160 to the row driver 222 or the column driver 224. The row driver 222 is configured to drive signals to the communication lines 215 that are horizontally integrated within the garment 110 while the column driver 224 is configured to drive signals to the communication lines 215 that are vertically integrated within the garment 110. When the communication lines 215 are arranged in the coordinate system 220 on the garment 110, the attachment mechanisms of the garment 110 may be positioned at coordinate points where a horizontal communication line and a vertical communication line intersect. In some embodiments, such as when the communication network 165 is an RF communication network, the attachment mechanisms may also be positioned at open areas between the communication lines 215 rather than or in addition to at intersection points.

Figure 6:
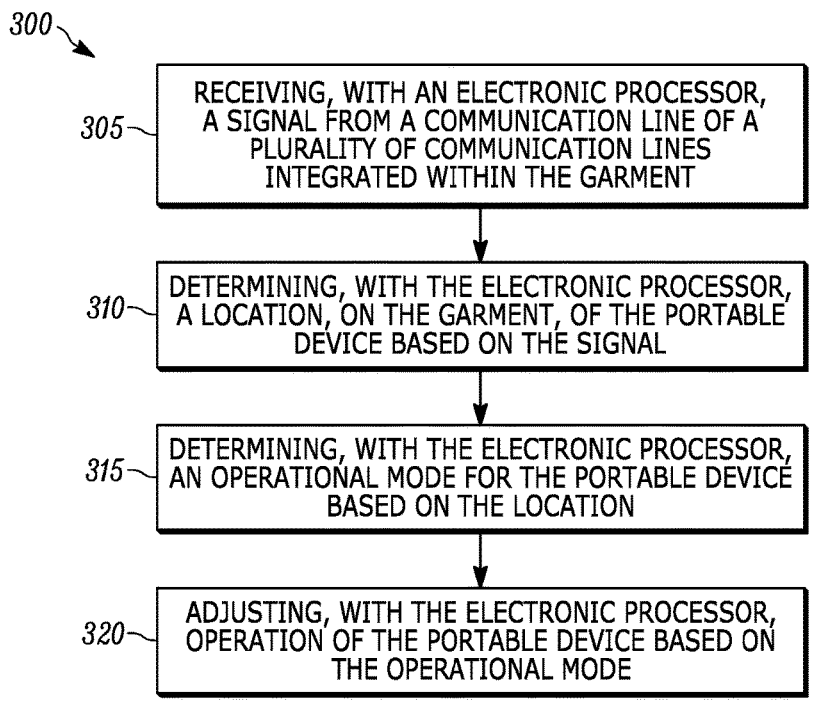
FIG. 6 is a flowchart of a method for locating and operating a portable device mounted to a garment performed by the system of FIG. 1 according to one embodiment.

FIG. 6 is a flowchart of a method 300 for locating and operating a portable device 105 mounted on a garment 110 performed by the system 100 of FIG. 1 according to one embodiment. In the example illustrated, the method 300 includes receiving, with the device electronic processor 140, a signal from the communication network 165 integrated within the garment 110 (at block 305). In some embodiments, the garment controller 160 generates the signal based on the routing data 185 stored in the garment memory 175. For example, the signal generated by the garment controller 160 may include an indication of a communication line 215 from among the communication lines 215. The garment controller 160 transmits the signal to the communication network 165 via the garment communication interface 180. The signal router 200 of the communication network 165 routes the signal to a communication line 215 based on the indication of a communication line 215 included in the signal. The communication line 215, in which the signal router 200 routed the signal to, transmits the signal to the portable device 105 (in example, the device electronic processor 140) via the communication interface 135 of the portable device 105.

The garment controller 160 may generate and transmit more than one signal. In some embodiments, the garment controller 160 generates and transmits a signal for each of the garment locations 218A through 218D. For example, with reference to FIG. 2, the garment controller 160 may generate a first signal with an identification of the garment location 218A, a second signal with an identification of the garment location 218B, a third signal with an identification of the garment location 218C, and a fourth signal with an identification of the garment location 218D. The garment controller 160 may transmit the first signal, the second signal, the third signal, and the fourth signal to the signal router 200 of the communication network 165. The signal router 200 routes the first signal to the first garment location 218A via the communication line 215 associated with the first garment location 218A. The signal router 200 similarly routes the second signal, the third signal, and the fourth signal to the appropriate garment locations 218B through 218D, respectively, via the communication lines 215 associated with each of the garment locations 218B through 218D.

In other embodiments, the garment controller 160 generates and transmits a signal for each of the communication lines 215. For example, with reference to FIG. 5, the garment controller 160 may generate a signal for each of the communication lines 215 in the coordinate system 220, where each signal includes an indication of each of the communication lines 215 in the coordinate system 220. The garment controller 160 transmits each of the signals to the signal router 200. The signal router 200 routes each of the signals (via the row driver 222 and the column driver 224) to the communication line 215 associated with the indication included in each of the signals. For example, the signal router 200 routes a signal with an indication of "y2" to the communication line 215 associated with the indication of "y2."

In some embodiments, the garment controller 160 generates and transmits the signal via a communication line 215 of the communication network 165 to the device electronic processor 140, as described above with respect to block 305 of FIG. 6, periodically at specific intervals. The specific intervals may be fixed or variable. For example, the garment controller 160 may generate a first signal to the garment location 218A, a second signal to the garment location 218D, delay for a certain time period, and then repeat, such that the garment controller 160 cyclically sends signals to each of the communication lines 215. Alternatively or in addition, the garment controller 160 may generate and transmit the signal via a communication line 215 of the communication network 165 to the device electronic processor 140 when a request from the portable device 105 is received. The request from the portable device 105 may be communicated via the communication interface 135 to the garment controller 160 using a communication line 215 of the communication network 165. For example, the user of the portable device 105 may initiate the request using the display 119 of the portable device 105, the hard keys 120 of the portable device 105, or the like. Once the user of the portable device 105 initiates the request, the request is transmitted to the garment controller 160 using a communication line 215 of the communication network 165. Alternatively or in addition, the garment controller 160 may generate and transmit the signal via a communication line 215 of the communication network 165 to the device electronic processor 140 when a change in status of the portable device 105 is detected, such as the attachment of the portable device 105 or the removal of the portable device 105 from the garment 110.

When the device electronic processor 140 receives the signal from the communication network 165, the device electronic processor 140 determines a location, on the garment 110, of the portable device 105 based on the signal (at block 310). As noted above, in some embodiments, the signal received by the device electronic processor 140 includes an indication of the communication line 215 upon which the signal was transmitted to the portable device 105. Based on the indication included in the signal, the device electronic processor 140 determines the location, on the garment 110, of the portable device 105. In some embodiments, the device electronic processor 140 determines the location, on the garment 110, of the portable device 105, by accessing the mapping data 148 stored in the device memory 145. For example, as noted above, the mapping data 148 may include a lookup table. Accordingly, the device electronic processor 140 may look up the indication included in the signal to determine a location, on the garment 110, associated with that indication. For example, with reference to FIG. 2, when the device electronic processor 140 receives a signal with an indication associated with the garment location 218B, the device electronic processor 140 may determine that the portable device is located at the garment location 218B. The mapping data 148 may store additional lookup tables, each associated with a different garment type or size. A received user input via the display 119 or a received garment indication signal received over the communication network 165 may be used by the device electronic processor 140 to select the associated lookup table for the garment 110.

Figure 7:
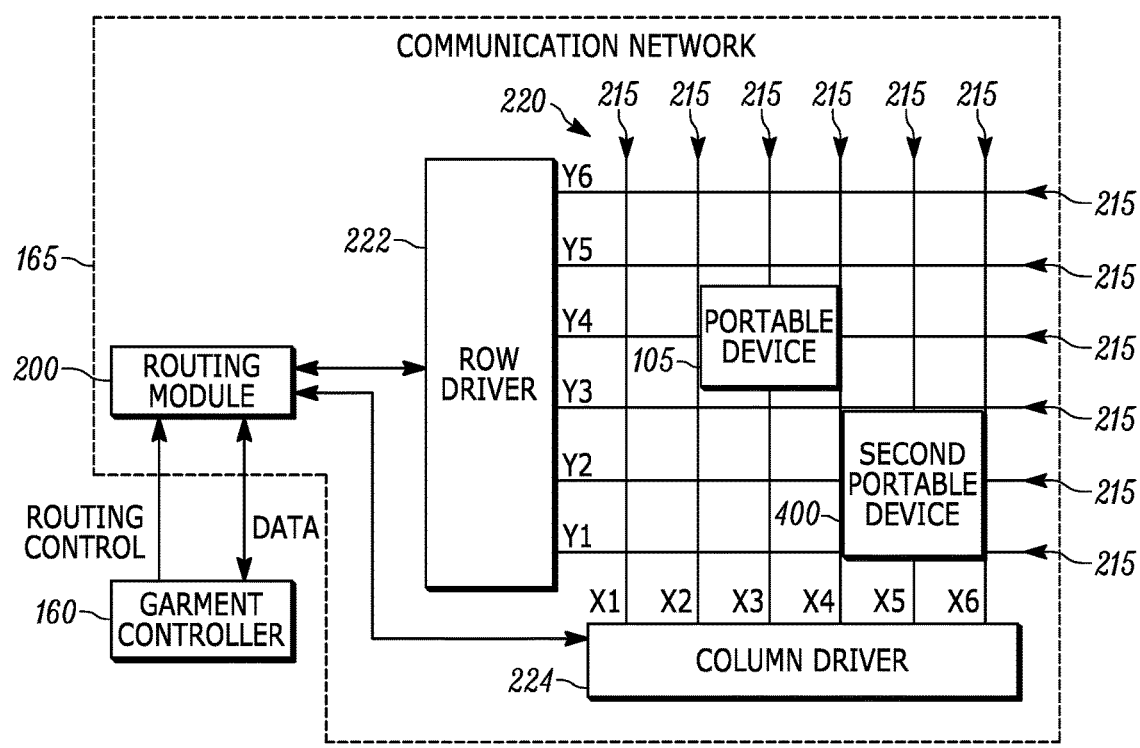
FIG. 7 is a diagram of the communication network of FIG. 5 when a portable device is mounted to the garment according to one embodiment.

As noted above, in some embodiments, the device electronic processor 140 receives more than one signal, such as a first signal and a second signal. The device electronic processor may determine the location, on the garment 110, of the portable device 105 looking up the indication included in the first signal and the indication included in the second signal. Based on the indication included in the first signal and the indication included in the second signal, the device electronic processor 140 may determine a coordinate point on the coordinate system 220 on the garment 110. As noted above, the coordinate point may represent a point of intersection or overlap of the two communication lines 215 associated with the first signal and the second signal. In some embodiments, the coordinate point is associated with the location, on the garment 110, of the portable device 105. For example, as illustrated in FIG. 7, the device electronic processor 140 may receive a first signal with "y4" as the indication and a second signal with "x3" as the indication. Based on the indication of the first signal and the indication of the second signal, the device electronic processor 140 may determine that the location, on the garment 110, of the portable device 105, is the coordinate point on the coordinate system 220 represented by (3, 4).

Based on the location, on the garment 110, of the portable device 105, the device electronic processor 140 determines an operational mode for the portable device 105 (at block 315). For example, the device electronic processor 140 may determine a first operational mode for the portable device 105 when the portable device 105 is at a first location on the garment 110. However, the device electronic processor 140 may determine a second operational mode for the portable device 105 when the portable device 105 is at a second location on the garment 110.

Once the device electronic processor 140 determines the operational mode for the portable device 105, the device electronic processor 140 adjusts operation of the portable device 105 based on the determined operational mode (at block 320). In some embodiments, the device electronic processor 140 adjusts operation of the portable device 105 by adjusting the configuration of the display 119 of the portable device 105, the configuration of the hard keys 120 of the portable device 105, or a combination thereof. Alternatively or in addition, the device electronic processor 140 adjusts the operation of the portable device 105 by adjusting the filtering or gain of the microphone 117 of the portable device 105 to customize audio settings for the particular location determined in block 310 of FIG. 6.

Alternatively or in addition, the device electronic processor 140 may adjust the operation of the portable device 105 by selecting a sensor or transducer from among a plurality of sensors or transducers based on the location determined in block 310 of FIG. 6. For example, the portable device 105 may include a remote speaker microphone (for example, the speaker 118 and the microphone 117) having multiple microphone elements. The device electronic processor 140 may adjust the number of microphone elements turned on or off based on the location, on the garment 110, of the portable device 105. For example, when the device electronic processor 140 determines the location, on the garment 110, of the portable device 105 to be a location on the garment 110 associated with a left shoulder of a user, the device electronic processor 140 may adjust the operation of the portable device 105 by turning on a subset of microphone elements positioned closest to a mouth of the user. The device electronic processor 140 may also adjust the operation of the portable device 105 by turning off a subset of microphone elements positioned farthest from a mouth of the user to prevent the portable device 105 from picking up background noise. The device electronic processor 140 may also adjust the operation of the portable device 105 by adjusting beamforming to focus audio capture by the microphone 117 towards the mouth of the user.

In some embodiments, a second portable device 400, in addition to the portable device 105, is mounted to the garment 110, as illustrated in FIG. 7. The second portable device 400 is similar to the portable device 105. When the garment 110 has multiple mounted devices, the mounted devices may communicate with each other (for example, via the communication network 165 of the garment 110). For example, the location of the second portable device 400 is determined by the second portable device 400 (for example, using the method 300), provided to the garment controller 160, and stored in the garment memory 175 of the garment 110. The portable device 105 communicates with the garment controller 160 (via the communication network 165) to determine the location of the second portable device 400. After the portable device 105 determines the location of the second portable device 400, the portable device 105 may communicate directly with the second portable device 400 (via the communication network 165). In some embodiments, the communication network 165 (the signal router 200) may perform the routing of the communication between the portable device 105 and the second portable device 400. This direct communication among devices mounted to the garment 110, which tend to be battery-powered, does not require a mounted device to monitor communication transmitted on a shared communication bus that is not intended for that mounted device. For example, the portable device 105 may transmit a routing request to the garment controller 160. The routing request may include a routing configuration for the signal router 200. The routing configuration may enable direct communication between the portable device 105 and the second portable device 400. Alternatively or in addition, the portable device 105 may address a signal for the second portable device 400. When the portable device 105 transmits the signal (via the communication network 165), the additional portable devices, such as the second portable device 400, a third portable device, and a fourth portable device, mounted to the garment 110 are only required read the address of the signal. Therefore, additional portable devices, such as a third portable device and a fourth portable device, are only required to read the address of the signal as opposed to the entire signal while only the second portable device 400 is required to read the entire signal.

Alternatively or in addition, the device electronic processor 140 may determine the operational mode of the portable device 105 based on the location of the second portable device 400. For example, when executing the method 300, the portable device 105 determines the location of the second portable device 400 as part of block 310, and, in block 315, determines an operational mode for the portable device 105 based on the location of the second portable device 400 in addition to or instead of based on the location of the portable device 105 on the garment 110.

In some embodiments, the spacing of the communication lines 215 may be adjusted based on a desired granularity or resolution, a size of the portable device 105, a method of mounting the portable device 105 to the garment 110, and the like. Depending on the spacing of the communication lines 215, the portable device 105 may receive multiple signals associated with one axis of the coordinate system 220. For example, when the device electronic processor 140 receives signals from two adjacent communication lines 215, the device electronic processor 140 may determine the location, on the garment 110, of the portable device 105 is between those two adjacent communication lines 215.

In some embodiments, the device electronic processor 140 also receives at least one user characteristic when the device electronic processor 140 receives the signal at block 305 of FIG. 6. The user characteristic indicates a characteristic of a user of the garment 110. The user characteristic may indicate a physical trait of a user, such as a dominate hand, a height, a gait, a medical condition, and the like. The user characteristic may indicate a preference of a user. For example, the user characteristic may indicate that the user prefers audible feedback as opposed to non-audible feedback. The user characteristic may include identification information, authorization information, or a combination thereof. For example, the user characteristic may include a username, a user identification number, a user profile, a security credential, and the like.

In some embodiments, the user characteristic is stored in the garment memory 175 of the garment 110. When the user characteristic is stored on the garment memory 175 of the garment 110, the garment controller 160 may transmit the user characteristic to the device electronic processor 140 using the communication network 165. However, alternatively or in addition, the user characteristic may be stored on the device memory 145. Alternatively or in addition, the user characteristic may be stored on and read from a smart card or a smart identification using, for example, near-field communication. The smart card or the smart identification card may be associated with and carried by a particular user. In some embodiments, the garment controller 160 reads the smart card using the communication network 165 and temporarily stores data of the smart card in the garment memory 175. When the portable device 105 is in communication with the garment controller 160 (via the communication network 165), the garment controller 160 may transmit the data of the smart card to the portable device 105.

The device electronic processor 140 may use the user characteristic to determine the operational mode for the portable device 105. For example, when executing the method 300, the device electronic processor 140 receives the user characteristic prior to determining the operational mode for the portable device 105 at block 315, and, in block 315, the device electronic processor 140 determines the operational mode for the portable device 105 based on the user characteristic in addition to or instead of based on the location of the portable device 105 on the garment 110. For example, the user characteristic may indicate that a user of the garment 110 is right-handed. The device electronic processor 140 may determine an operational mode for the portable device 105 specific to a right-handed user, such as configuring the display 119 of the portable device 105, the hard keys 120 of the portable device 105, or a combination thereof for a right-handed user. In another example, the user characteristic may indicate a credential of a user of the garment 110, such as a credential indicating that the user of the garment 110 is a supervisory user. The device electronic processor 140 may determine the operational mode for the portable device 105 to include functionality available to a user with the indicated credential, such as functionality restricted to a supervisory user.

Alternatively or in addition, the device electronic processor 140 also receives a garment characteristic when the device electronic processor 140 receives the signal at block 305 of FIG. 6. The garment characteristic indicates a characteristic of the garment 110. For example, in some embodiments, the garment characteristic includes a type of garment 110, such as a vest, a long-sleeved vest, and the like. In some embodiments, the garment characteristic is stored in the garment memory 175 of the garment 110. When the garment characteristic is stored on the garment memory 175 of the garment 110, the garment controller 160 transmits the garment characteristic to the device electronic processor 140 using the communication network 165. Alternatively or in addition, the garment characteristic is stored on and read from a smart card or a smart identification associated with the garment 110 using, for example, near-field communication. The device electronic processor 140 uses the garment characteristic to determine the operational mode of the portable device 105. For example, when executing the method 300, the device electronic processor 140 receives the garment characteristic prior to determining the operational mode for the portable device 105 at block 315, and, in block 315, the device electronic processor 140 determines the operational mode for the portable device 105 based on the garment characteristic in addition to or instead of based on the location of the portable device 105 on the garment 110. For example, the garment characteristic may indicate that the garment 110 is a vest. The device electronic processor 140 then determines a first operational mode tailored to a vest. For example, when the portable device 105 is a body-worn video camera (in example, that includes the image sensor 116), the device electronic processor 140 may determine an operational mode for the portable device 105 in which the field of view of the portable device 105 is adjusted upward (in example, a first operational mode). However, when the portable device 105 is a body-worn video camera (in example, that includes the image sensor 116) and the garment characteristic indicates that the garment 110 is a helmet, the device electronic processor 140 may determine an operational mode for the portable device 105 in which the field of view of the portable device 105 is adjusted downward (in example, a second operational mode).

In another example, the garment characteristic indicates that the garment 110 is a vest and the portable device 105 is a remote speaker microphone (for example, the microphone 117 and the speaker 118). The device electronic processor 140 determines an operational mode for the portable device 105 associated with a first operational mode for a remote speaker microphone. In this first operational mode, a primary radio in a separate housing may provide audio input to the microphone 117 and audio output from the speaker 118. However, when the garment characteristic indicates that the garment 110 is a pair of pants, the device electronic processor 140 determines a second operational mode for the portable device 105 in which the remote speaker microphone is disabled and the functionality of the remote speaker microphone is reverted to the primary radio.

In yet another example, the garment characteristic indicates that the garment 110 is a vest and the portable device 105 includes annunciation functionality, such as light feedback, audio feedback, and haptic feedback provided by the display 119, the speaker 118, or a combination thereof. The device electronic processor 140 determines an operational mode for the portable device 105 in which light feedback is provided to a user of the garment 110 (in example, a first operational mode). However, when the garment characteristic indicates that the garment 110 is a helmet, the device electronic processor 140 determines an operational mode for the portable device 105 in which audio feedback is provided to a user of the garment 110 (in example, a second operational mode).

In some embodiments, as noted above, the portable device 105 includes an orientation sensor 121. The orientation sensor 121 may be configured to determine an orientation of the portable device 105 when the portable device 105 is mounted to the garment 110. For example, the orientation sensor 121 may detect that the portable device 105 is mounted upside down on the garment 110. As noted above, the orientation of the portable device 105 when mounted to the garment 110 may affect a user's interaction with the portable device 105, the functionality of the portable device 105, or a combination thereof. Accordingly, the device electronic processor 140 may use the orientation data collected by the orientation sensor 121 of the portable device 105 to determine the operational mode of the portable device 105. For example, when executing the method 300, the device electronic processor 140 receives the orientation data collected by the orientation sensor 121 prior to the device electronic processor 140 determining the operational mode for the portable device 105 at block 315, and, in block 315, the device electronic processor 140 determines the operational mode for the portable device 105 based on the orientation data in addition to or instead of based on the location of the portable device 105 on the garment 110.

In some embodiments, the garment 110 includes a plurality of tags, such as near-field communication (NFC) tags. The plurality of tags may be integrated within the garment 110 at various predetermined locations on the garment 110. For example, the plurality of tags may be centrally positioned at each attachment mechanism of the garment 110. Each of the plurality of tags may include a location descriptor identifying a location on the garment 110. Accordingly, when the portable device 105 is attached via an attachment mechanism of the garment 110, the portable device 105 (for example, the communication interface 135 of the portable device 105) may "read" the location descriptor of the tag integrated within the garment 110 at the location of that attachment mechanism of the garment 110. The device electronic processor 140 may determine the location, on the garment 110, of the portable device 105 based on the location descriptor of the tag. For example, when executing the method 300, the device electronic processor 140 receives the location descriptor prior to the device electronic processor 140 determining the operational mode for the portable device 105 at block 315, and, in block 315, the device electronic processor 140 determines the operational mode for the portable device 105 based on the location descriptor. In some embodiments, the garment 110 is manufactured with a plurality of "blank" tags. At a later point in time (for example, as an automated final manufacturing step) the garment 110 may be programmed to encode each of the plurality of tags with an associated location descriptor.

In some embodiments, the garment 110 is available in various sizes, such as sizes ranging from small to large. The surface area of the garment 110 varies depending on the size thereof. Accordingly, using the same number of communication lines 215 in a small garment 110 and a large garment 110 results in a difference in resolution. In some embodiments, it is desirable to address such a resolution difference without placing an undue burden on the portable device 105 mounted to the garment 110, without adding unnecessary cost to the garment 110, and without sacrificing reliability. In some embodiments, various scaling techniques may be applied to address the potential for resolution differences for differently sized garments 110.

For example, ranges of coordinates for various portions of the garment 110 may be defined. For example, communication lines 215 associated with the unique identifiers ranging between "x0" and "x10" may be dedicated to the left side portion of garments and communication lines 215 associated with the unique identifiers ranging between "x11" and "x20" may be dedicated to the right side portion of garments. During the design of the garment 110, the number of communication lines 215 routed to a selected portion of the garment 110 may be determined based on the size of the garment 110 and the desired resolution. For example, for a small sized garment 110, the left front portion may include four of the communication lines 215, which may be associated with the indications "x0," "x3," "x6," and "x9," to provide a certain level of resolution. However, for a large sized garment 110, the left front portion may include six of the communication lines 215, which may be associated with the unique identifiers "x0," "x2," "x4," "x6," "x8," and "x10," to achieve a comparable resolution as the small sized garment 110.

In some embodiments, the garment 110 includes multiple sets of communication lines 215. Each set of communication lines 215 may exist on the garment 110 for unrelated purposes. For example, a first set of communication lines 215 within the garment 110 may be used for general communication throughout the garment 110 while a second set of communication lines 215 within the garment 110 may be used for device location communication between the garment controller 160 and the portable device 105, as described herein. General communication may relate to the communication between various devices and sensors integrated within or mounted to the garment 110. Having multiple sets of communication lines 215 within the garment 110 allows for each set of communication lines 215 to be customized based on a specific purpose or requirements for each set of communication lines 215. However, in other embodiments, the communication lines 215 provide both general communication and device location communication.

In some embodiments, the method 300 further includes (after block 320) determining, with the device electronic processor 140, when the portable device 105 is removed from the garment 110 and adjusting, with the device electronic processor 140, the operation of the portable device 105 when the portable device 105 is removed from the garment 110. For example, the device electronic processor 140 may generate an attachment confirmation request signal and transmit the attachment confirmation request signal via the communication network 165 to the garment electronic processor 170. In response to receiving the attachment confirmation request signal, the garment electronic processor 170 may generate an attachment confirmation signal and transmit the attachment confirmation signal to the device electronic processor 140 (via the communication network 165). When the device electronic processor 140 receives the attachment confirmation signal from the garment electronic processor 170, the device electronic processor 140 determines that the portable device 105 has not been removed from the garment 110. When the device electronic processor 140 does not receive the attachment confirmation signal from the garment electronic processor 170 (for example, within a predetermined period of time), the device electronic processor 140 determines that the portable device 105 has been removed from the garment 110. In response to determining that the portable device 105 has been removed from the garment 110, the device electronic processor 140 may adjust the operation of the portable device 105. For example, the portable device 105 may be a remote speaker microphone (in example, the speaker 118 and the microphone 117). When the device electronic processor 140 determines that the portable device 105 was removed from the garment 110, the device electronic processor 140 adjusts the operation of the portable device 105 by disabling its speaker 118 and microphone 117 to revert functionality of the portable device 105 to a primary radio (in example, the second portable device 400) mounted to the garment 110. Alternatively, the portable device 105 is a portable radio that includes a remote speaker microphone (in example, the speaker 118 and the microphone 117) in a first housing with the communication interface 135. The remote speaker microphone is coupled via a wired connection or wireless connection to the device electronic processor 140, which is separately housed in a local speaker and microphone. Upon determining that the remote speaker microphone was removed from the garment 110, using techniques described herein, the device electronic processor 140 disables the remote speaker microphone and reverts functionality of the remote speaker microphone to the local speaker and microphone.

In some embodiments, the device electronic processor 140 generates and transmits the attachment confirmation request signal periodically, such as every second, every minuet, or another time period. Alternatively or in addition, the device electronic processor 140 may generate and transmit the attachment confirmation request signal in response to a trigger, such as a detected impact of the portable device 105. For example, the orientation sensor 121 of the portable device 105 may include an accelerometer. Based on the data collected by the accelerometer, the device electronic processor 140 determines when the portable device 105 experiences a sudden impact (for example, falling off the garment 110 and landing on the ground). Accordingly, in some embodiments, the device electronic processor 140 generates and transmits the attachment confirmation request signal based on a comparison of an acceleration of the portable device 105 to a predetermined threshold. For example, when an acceleration of the portable device 105 exceeds a predetermined threshold, the device electronic processor 140 generates and transmits the attachment confirmation request signal.

In some embodiments, as part of block 315 of FIG. 6, the device electronic processor 140 determines the operational mode for the portable device 105 based a garment characteristic, an orientation of the portable device 105, a user characteristic, whether the portable device 105 is attached to the garment 110, or a combination thereof in addition to or instead of based on the location, on the garment 110, of the portable device 105. In other words, the device electronic processor 140 may determine the operational mode for the portable device 105 based on the location, on the garment 110, of the portable device 105 and at least one additional parameter. When the device electronic processor 140 determines the operational mode for the portable device 105 based on the location, on the garment 110, of the portable device 105 and at least one additional parameter, the device electronic processor 140 may adjust operation of the portable device 105 by, for example, adjusting a configuration of the display 119, adjusting a configuration of the hard keys 120, adjusting a field of view of the image sensor 116, disabling a function, enabling a function, adjusting a source of annunciation feedback, adjusting beamforming for the microphone 117, adjusting filtering for the microphone 117, adjusting a gain for the microphone 117, or a combination thereof.

As one example, the device electronic processor 140 determines the operational mode for the portable device 105 based on the location, on the garment 110, of the portable device 105 and the orientation of the portable device 105. For example, the device electronic processor 140 determines that the location, on the garment 110, of the portable device 105 is associated with a left shoulder of a user of the garment 110 and that the orientation of the portable device 105 is upside down. In response, the device electronic processor 140 adjusts operation of the portable device 105 by, for example, enabling (turning on) a first subset of microphone elements positioned closest to a mouth of the user and disabling (turning off) a second subset of microphone elements positioned farthest from a mouth of the user. However, when the device electronic processor 140 determines that the location, on the garment 110, of the portable device 105 is associated with a right shoulder of the user of the garment 110 and that the orientation of the portable device 105 is upside down, the device electronic processor adjusts operation of the portable device 105 by, for example, disabling the first subset of microphone elements (as the first subset of microphone elements are now positioned farther from the mouth of the user) and enabling the second subset of microphone elements (as the second subset of microphone elements are now positioned closer to the mouth of the user). Similarly, when the device electronic processor 140 determines that the location, on the garment 110, of the portable device 105 is associated with the right shoulder of the user of the garment 110 and that the orientation of the portable device 105 is right-side up, the device electronic processor adjusts operation of the portable device 105 by, for example, enabling the first subset of microphone elements (as the first subset of microphone elements are now positioned closer to the mouth of the user) and disabling the second subset of microphone elements (as the second subset of microphone elements are now positioned farther from the mouth of the user).

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

I claim:

1. A method for locating and operating a portable device mounted to a garment, the method comprising:
receiving, with an electronic processor, a signal from a communication line of a plurality of communication lines integrated within the garment;
determining, with the electronic processor, a location, on the garment, of the portable device based on the signal;
determining, with the electronic processor, an operational mode for the portable device based on the location; and
adjusting, with the electronic processor, operation of the portable device based on the operational mode.

2. The method of claim 1, wherein receiving the signal includes receiving an indication of the communication line over which the signal was transmitted from among the plurality of communication lines of the garment.

3. The method of claim 1, wherein receiving the signal includes receiving a first signal from the communication line and a second signal from a second communication line different from the communication line, wherein the plurality of communication lines are arranged to form a coordinate system within the garment.

4. The method of claim 3, wherein determining the location includes determining a coordinate point on the coordinate system based on the first signal and the second signal, wherein the coordinate point is associated with the location, on the garment, of the portable device, and wherein the first signal indicates a row of the coordinate system and the second signal indicates a column of the coordinate system.

5. The method of claim 1, further comprising receiving at least one selected from a group consisting of a user characteristic indicating a characteristic of a user of the garment, orientation data from an orientation sensor associated with the portable device, and a garment characteristic indicating a characteristic of the garment,
wherein determining the operational mode for the portable device includes determining the operational mode for the portable device based on at least one selected from the group consisting of the user characteristic indicating a characteristic of a user of the garment, the orientation data from an orientation sensor associated with the portable device, the garment characteristic indicating a characteristic of the garment, and a determination that the portable device has detached from the garment.

6. The method of claim 5, wherein adjusting the operation of the portable device includes at least one selected from a group consisting of adjusting a configuration of a display, adjusting a configuration of a hard key, adjusting a field of view of an image sensor, disabling a microphone, enabling the microphone, adjusting a source of annunciation feedback, adjusting beamforming for a microphone, adjusting filtering for the microphone, and adjusting a gain for the microphone.

7. A portable device mounted to a garment, the portable device comprising:
a memory storing instructions; and
an electronic processor that is coupled to the memory and, through execution of the instructions, is configured to
receive a signal from a communication line of a plurality of communication lines integrated within the garment,
determine a location, on the garment, of the portable device based on the signal,
determine an operational mode for the portable device based on the location, and
adjust operation of the portable device based on the operational mode.

8. The portable device of claim 7, wherein the signal includes an indication of a communication line over which the signal was transmitted from among a plurality of communication lines of the garment.

9. The portable device of claim 7, wherein the signal includes a first signal from the communication line among the plurality of communication lines of the garment and a second signal from a second communication line among the plurality of communication lines of the garment, the second communication line different from the communication line, and wherein the first signal and the second signal indicate a coordinate point on a coordinate system formed by the plurality of communication lines integrated within the garment.

10. The portable device of claim 7, wherein the electronic processor is further configured to receive a user characteristic, the user characteristic indicating a characteristic of a user of the garment, and determine the operational mode for the portable device based on the user characteristic.

11. The portable device of claim 7, wherein the electronic processor is further configured to receive orientation data from an orientation sensor associated with the portable device and determine the operational mode for the portable device based on the orientation data.

12. The portable device of claim 7, wherein the electronic processor is further configured to receive a garment characteristic, the garment characteristic indicating a characteristic of the garment, and determine the operational mode for the portable device based on the garment characteristic.

13. The portable device of claim 7, wherein the signal includes a location descriptor from a tag associated with a predetermined location on the garment.

14. A system for locating and operating a portable device, the system comprising:
a garment having a communication line of a plurality of communication lines integrated within the garment, the garment including an electronic processor configured to generate and transmit a signal; and
a portable device mounted to the garment, the portable device including a second electronic processor configured to
receive the signal from the communication line integrated within the garment,
determine a location, on the garment, of the portable device based on the signal,
determine an operational mode for the portable device based on the location, and
adjust operation of the portable device based on the operational mode.

15. The system of claim 14, wherein the signal includes an indication of the communication line over which the signal was transmitted from among the plurality of communication lines integrated within the garment.

16. The system of claim 14, wherein the second electronic processor is further configured to receive a second signal associated with a second portable device mounted to the garment, the second signal indicating a second location, on the garment, of the second portable device, wherein the second electronic processor is configured to determine the operational mode for the portable device based on the second location, on the garment, of the second portable device.

17. The system of claim 14, wherein the plurality of communication lines integrated within the garment are arranged to form a coordinate system within the garment.

18. The system of claim 17, wherein the signal includes a first signal from the communication line among the plurality of communication lines and a second signal from a second communication line among the plurality of communication lines, the second communication line different from the communication line, and wherein the first signal and the second signal indicate a coordinate point on the coordinate system.

19. The system of claim 14, wherein the second electronic processor is further configured to receive at least one selected from a group consisting of a user characteristic indicating a characteristic of a user of the garment, orientation data from an orientation sensor associated with the portable device, a garment characteristic indicating a characteristic of the garment.

20. The system of claim 19, wherein the second electronic processor is further configured to determine the operational mode for the portable device based on at least one selected from the group consisting of the user characteristic indicating a characteristic of a user of the garment, the orientation data from an orientation sensor associated with the portable device, and the garment characteristic indicating a characteristic of the garment.

\* \* \* \* \*